US008895505B2

(12) United States Patent
Paspaliaris et al.

(10) Patent No.: US 8,895,505 B2
(45) Date of Patent: Nov. 25, 2014

(54) METHOD OF TREATMENT OF TYPE 2 DIABETES

(75) Inventors: Vasilis Paspaliaris, Malvern East (AU); James Thornton, Makati (PH)

(73) Assignee: AdiStem Ltd., Hong Kong (HK)

( * ) Notice: Subject to any disclaimer, the term of this patent is extended or adjusted under 35 U.S.C. 154(b) by 0 days.

(21) Appl. No.: 13/509,177

(22) PCT Filed: Nov. 10, 2010

(86) PCT No.: PCT/AU2010/001496
§ 371 (c)(1),
(2), (4) Date: Dec. 21, 2012

(87) PCT Pub. No.: WO2011/057326
PCT Pub. Date: May 19, 2011

(65) Prior Publication Data
US 2013/0090289 A1 Apr. 11, 2013

(30) Foreign Application Priority Data
Nov. 10, 2009 (GB) .................................. 0919603.1

(51) Int. Cl.
| A61K 38/08 | (2006.01) |
| A61K 38/10 | (2006.01) |
| C07K 7/00 | (2006.01) |
| A61P 3/10 | (2006.01) |
| A61K 38/22 | (2006.01) |

(52) U.S. Cl.
CPC ............. *A61K 38/2292* (2013.01); *A61K 38/08* (2013.01)
USPC ............................ 514/6.9; 530/326; 530/329

(58) Field of Classification Search
CPC ........................... A61K 38/2292; A61K 38/08
See application file for complete search history.

(56) References Cited

U.S. PATENT DOCUMENTS

| 4,388,234 | A | 6/1983 | Horecker |
| 6,150,117 | A | 11/2000 | Zetter et al. |
| 2006/0100156 | A1 | 5/2006 | Hannappel et al. |
| 2006/0264360 | A1 | 11/2006 | Girardi et al. |

FOREIGN PATENT DOCUMENTS

| EP | 1908779 A1 | 4/2008 | |
| WO | WO-00/06190 A1 | 2/2000 | |
| WO | WO-01/85767 A2 | 11/2001 | |
| WO | WO-2007/132291 A2 | 11/2007 | |
| WO | WO-2008/024194 A2 | 2/2008 | |
| WO | WO-2008/045345 A2 | 4/2008 | |
| WO | WO-2009/046848 A1 | 4/2009 | |
| WO | WO 2009/046848 A1 * | 4/2009 | ............. A61K 38/17 |

OTHER PUBLICATIONS

Mealey, Periodontal disease and diabetes, JADA, 2006, 137, pp. 26S-31S.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Inflammatory pathway, from http://www.biocarta.com/pathfiles/h_inflampathway.asp, p. 1, accessed Feb. 18, 2014.*
Thymosin beta 4, from http://www.ncbi.nlm.nih.gov/protein/NP_066932.1, pp. 1-3, accessed Mar. 26, 2014.*
International Search Report and Written Opinion of the International Searching Authority from parent PCT application PCT/AU2010/001496 dated Feb. 18, 2011.
Anonymous, "AdiStem Peptide TB4-7", pp. 1-4, online from http://web.archive.org/web/20091024060910; http://www.adistem.com/peptide.html, Oct. 24, 2009.
Anonymous, "AdiStem Pops the Fat Stem Cell Cork in France | PRLog", pp. 1-2, online from http://www.prlog.org/10137462-adistem-pops-the-fat-stem-cell-cork-in-france.html, Nov. 6, 2008.
Anonymous, "AdiStem TB4-7 Peptide", pp. 1-7, online from http://immortalhair.forumandco.com/t2559-adistem-tb4-7-peptide, Feb. 15, 2010.
Anonymous, "IFATS08 Abstract Presenters", pp. 1-9; online from http://web.archive.org/web/20080928222757/http://www.ifats08.org/ifats08-abstract-presenters.html, Sep. 28, 2009.
Anonymous, "NCT00598871 on Feb. 25, 2009: ClinicalTrials.gov Archive", pp. 1-3, online from http://clinical trials.gov/archive/NCT0, Feb. 25, 2009.
Anonymous, "News and Highlights from Week 52, Dec. 25, 2009", *Current Patents Gazette*, 12(52):1-2, online from http://doczine.com/bigdata/1/1367259132_fd7c760343/news2009_cpg.pdf, Dec. 1 2009.
Anonymous, "Stem Cell Therapies | Stem Cell Therapy for Hair Growth", p. 1, online from http://web.archive.org/web/20100324031504/http://www.adistem.com/application/hair-growth.htm, Mar. 24, 2010.
Anonymous, "Stem Cell Therapy | AdiStem TB4-7 Peptide", online from http://web.archive.org/web/20100315032632/http://www.adistem.com/peptide.html, Mar. 15, 2010.
Database: Uniprot—Prothymosin alpha; terminally processed, thymosin alpha-1; accession No. P06454, Oct. 13, 2009.
Goldstein, A. L. et al., "Thymosin β4: actin-sequestering protein moonlights to repair injured tissues", *Trends in Molecular Medicine*, 11(9):421-429 (Elsevier Current Trends, Great Britain, Sep. 1, 2005).

(Continued)

*Primary Examiner* — Julie Ha
*Assistant Examiner* — Li Ni Komatsu
(74) *Attorney, Agent, or Firm* — Alan W. Steele; Foley Hoag LLP

(57) ABSTRACT

Provided is a method of treating type 2 diabetes in a subject, comprising administering a polypeptide comprising thymosin, or an active fragment or variant thereof, preferably comprising or consisting of the peptide LKKTETQ (SEQ ID NO: 1).

10 Claims, No Drawings

(56) References Cited

OTHER PUBLICATIONS

Hruby, V. J., "Designing peptide receptor agonists and antagonists", *Nature Reviews Drug Discovery*, 1(11):847-858 (Nature Publishing Group, USA, Nov. 1, 2002).

Philp, D., et al., "Thymosin $\beta_4$ and a synthetic peptide containing its actin-binding domain promote dermal wound repair in db/db diabetic mice and in aged mice", *Wound Repair and Regeneration*, 11(1):19-24 (Mosby-Year Book, St. Louis, MO, USA, Jan. 1, 2003).

Yang, et al., "Intraperitoneal co-administration of thymosin $\alpha$-1 ameliorates streptozotocin-induced pancreatic lesions and diabetes in C57BL/6 mice", *International Journal of Molecular Medicine*, 23(5):597-602 (Apr. 6, 2009).

Supplementary European Search Report from corresponding European application EP 10829343 dated Feb. 24, 2014.

\* cited by examiner

METHOD OF TREATMENT OF TYPE 2 DIABETES

RELATED APPLICATIONS

This application is the U.S. national phase of international patent application Serial No. PCT/AU2010/001496, filed Nov. 10, 2010, which claims benefit of priority from Great Britain Application No. 0919603.1, filed Nov. 10, 2009.

The present invention relates to methods of treating Type 2 diabetes.

BACKGROUND

Diabetes mellitus type 2 or type 2 diabetes (formerly called [non-[insulin]]-dependent diabetes mellitus (NIDDM), or adult-onset diabetes) is a disorder that is characterized by high blood glucose in the context of insulin resistance and relative insulin deficiency. While it is often initially managed by increasing exercise and dietary modification, medications are typically needed as the disease progresses. There are an estimated 23.6 million people in the U.S. (7.8% of the population) with diabetes with 17.9 million being diagnosed, 90% of whom are type 2. Prevalence rates doubled between 1990 and 2005, characterising the increase as an epidemic. Traditionally considered a disease of adults, type 2 diabetes is increasingly diagnosed in children in parallel to rising obesity rates due to alterations in dietary patterns and life styles during childhood. Complex and multifactorial metabolic changes brought about by type 2 diabetes very often lead to damage and function impairment of many organs, most importantly the cardiovascular system. This leads to substantially increased morbidity and mortality in both type 2 patients.

Insulin resistance means that body cells do not respond appropriately when insulin is present. Unlike type 1 diabetes mellitus, the insulin resistance is generally "post-receptor", meaning it is a problem with the cells that respond to insulin rather than a problem with production of insulin.

Type 2 diabetes may go unnoticed for years before diagnosis, since symptoms are typically milder (eg, no ketoacidosis, coma, etc) and can be sporadic. However, severe complications can result from improperly managed type 2 diabetes, including renal failure, blindness, slow healing wounds (including surgical incisions), and arterial disease, including coronary artery disease. The onset of type 2 diabetes has been most common in middle age and later life, although it is being more frequently seen in adolescents and young adults due to an increase in child obesity and inactivity.

Symptoms of Type 2 diabetes include: excessive urine production; excessive thirst and increased fluid intake; blurred vision; unexplained weight loss; lethargy; fatigue; changes in energy metabolism.

Type 2 diabetes is a chronic, progressive disease that has no established cure. However, there are some treatments which can delay the formerly inevitable consequences of the condition. Type 2 can initially be treated by adjustments in diet and exercise, and by weight loss, most especially in obese patients. Such "life style" treatments can be coupled with the use of diabetes medication, such as metformin (Glucophage), a diabetes medication that lowers glucose production in the liver. Along with metformin, other oral or injected medications can be used to treat type 2 diabetes: some diabetes medications stimulate the pancreas to produce and release more insulin; others block the action of enzymes that break down carbohydrates or make your tissues more sensitive to insulin. Some people who have type 2 diabetes need insulin therapy as well. Weight-loss related surgery can also be used, such as gastric bands.

Nevertheless, despite the disease treatment and management regimes outlined above, the healthcare costs of managing type 2 diabetes and the mortality rate worldwide highlights the need to develop improved medicines for the treatment of this disorder.

SUMMARY

A first aspect provides a method of treating type 2 diabetes in a subject, comprising administering a polypeptide comprising thymosin, or an active fragment or variant thereof.

A second aspect provides a polypeptide comprising thymosin, or an active fragment or variant thereof for use as a medicament for the prevention or treatment of type 2 diabetes.

An alternative second aspect provides use of a polypeptide comprising thymosin, or an active fragment or variant thereof in the manufacture of a medicament for treating type 2 diabetes.

A third aspect of the invention provides a method of treating type 2 diabetes comprising administering a composition comprising a peptidomimetic of thymosin, or an active fragment or variant thereof A fourth aspect provides a composition comprising a peptidomimetic of thymosin, or an active fragment or variant thereof for treating type 2 diabetes.

An alternative fourth aspect provides use of a composition comprising a peptidomimetic of thymosin or an active fragment of variant thereof in the manufacture of a medicament for treating type 2 diabetes.

In one embodiment of the first and second aspects the active fragment of thymosin is LKKTETQ (SEQ ID NO:1). In one embodiment of the first and second aspects the polypeptide comprises thymosin beta 4 or a fragment thereof comprising LKKTETQ (SEQ ID NO:1).

In one embodiment of the third or fourth aspects the peptidomimetic is based on the polypeptide LKKTETQ (SEQ ID NO:1). In one embodiment of the third and fourth aspects the peptidomimetic is based on thymosin beta 4 or a fragment thereof comprising LKKTETQ (SEQ ID NO:1).

DETAILED DESCRIPTION

Thymosin is family of a small polypeptides found in high quantity in thymus and spleen, but widely distributed in many tissues. Members of the thymosin family have been shown to bind to actin monomers and thus to inhibit actin polymerization. The physiological processes that these polypeptides affect include stimulation or suppression of immune responses, regulation of actin dynamics and cell motility, neuroplasticity, repair and remodeling of vessels of the heart and other injured tissues, angiogenesis, and stem cell differentiation.

A number of polypeptides are members of the thymosin family; the most abundant member of the family is thymosin beta 4 (Tβ4). It was first isolated as a thymic hormone that induces terminal deoxynucleotidyltransferase.

Until the present invention, it had not been disclosed or suggested that thymosin 134 or its active fragments such as LKKTETQ (SEQ ID NO: 1) could be used for the prevention or treatment of type 2 diabetes.

By "thymosin" we include polypeptides of the thymosin family. Members of the thymosin family include human thymosin beta 4 (X and Y chromosome); human thymosin beta 10; thymosin beta-4-like protein 1; thymosin beta-4-like protein 2; thymosin beta-4-like protein 3; thymosin beta-4-like protein 6; thymosin-like protein 8; thymosin like 4; any further members of the family from other species. Information concerning the members of the thymosin protein family may be readily obtained from, for example, UniProt (<http://www.uniprot.org>) where a search for 'thymosin' can be performed (<http://www.uniprot.org/uniprot/?query=thymosin&sort=score>). The UniProt database directly provides the amino acid sequence of the thymosin proteins. Further members of the thymosin protein family may also be located by database searching.

In one embodiment thymosin does not include thymosin fraction 5. A preferred embodiment of the first aspect of the invention is wherein the thymosin is thymosin beta 4. An example of the amino acid sequence of the thymosin beta 4 polypeptide encoded by the X-chromosomal gene is given below:
Thymosin Beta-4 (Swiss-Prot P62328)

```
                                          (SEQ ID NO: 2)
MSDKPDMAEI EKFDKSKLKK TETQEKNPLP SKETIEQEKQ AGES
```

Thymosin polypeptide can be routinely prepared using well known laboratory techniques. Also, there are a number of commercial sources of thymosin beta 4, which can be used in the invention.

By "an active fragment of thymosin" we include where the thymosin used as a medicament comprises less than the total amino acid sequence of the full native polypeptide; preferably the fragment is therapeutically effective, in that it retains its biological activity: in this case, its anti-type II diabetic property. The fragment can be any size and any part of the thymosin polypeptide; examples of representative fragments of thymosin are provided in the specification. For example, the fragment may be between 4 and 30 amino acids; 5 and 25 amino acids; 6 and 16; 7 and 15 amino acid residues.

By "a variant of thymosin" we include a peptide wherein at one or more amino acid positions, there are amino acid mutations selected from insertions, deletions, or substitutions, either conservative or non-conservative; preferably the variant is therapeutically effective in that such changes result in a protein whose properties (for example its anti-type II diabetic property; protein interaction; thermostability; activity in a certain pH-range (pH-stability)), have not significantly been changed. In one embodiment the variant comprises a mutation at one, two, three, four or five amino acid residues of Tβ4 or an active fragment thereof.

By "conservative substitutions" is intended combinations such as Gly, Ala; Val, Ile, Leu; Asp, Glu; Asn, Gln; Ser, Thr; Lys, kg; and Phe, Tyr. Such variants may be made using routine methods of protein engineering and site-directed mutagenesis as would be well known to those skilled in the art. Examples of representative variants of thymosin are provided in the specification.

In one embodiment variants are based on the consensus sequence $X_1LKX_2TX_3X_4X_5X_6$ (SEQ ID NO: 3), wherein X is any amino acid. Preferably X is a conservative substitution of the native amino acid of Tβ4 given in SEQ ID NO: 1.

In one embodiment $X_1$ is 1, 2, 3, 4, 5, 6, 7, 8, 9, 10, 11, 12, 13, 14 or 15 amino acid residues or is absent, $X_2$ is K, H or A, $X_3$ is E or N, $X_4$ is T or M, $X_5$ is Q, N, E or A and $X_6$ is 1, 2, 3, 4, 5, 6, 7, 8, 9, 10, 11, 12, 13, 14 or 15 amino acid residues or is absent.
Preferably $X_1$ comprises (F/L)(D/N)(S/A/T/K/N)(K/N/G)
Preferably $X_6$ comprises (E/T)(K/E)(N/E).

The polypeptide may comprise one of amino acid sequences:

| | |
|---|---|
| FDKSKLKKTETQEKN | (SEQ ID NO: 4) |
| FDKAKLKKTETQEKN | (SEQ ID NO: 5) |
| FDRSKLKKTETNTEE | (SEQ ID NO: 6) |
| FDKTKLKKTETQEKN | (SEQ ID NO: 7) |
| FDKSKLKKTNTEEKN | (SEQ ID NO: 8) |
| FDRSKLKKTNTEEKN | (SEQ ID NO: 9) |
| FDKTKLKKTETAEKN | (SEQ ID NO: 10) |
| FNRAKLKKTETQEKN | (SEQ ID NO: 11) |
| FNKAKLKKTEMQEKN | (SEQ ID NO: 12) |
| FDAKKLKHTETNEKN | (SEQ ID NO: 13) |
| FNQNNLKHTETNEKN | (SEQ ID NO: 14) |
| LDKAKLKATEMQEKN | (SEQ ID NO: 15) |
| FDKAGLKKTETEEKE. | (SEQ ID NO: 16) |

In a preferred embodiment the polypeptide is LKKTETQ (SEQ ID NO: 1) or comprises LKKTETQ (SEQ ID NO: 1) and up to 15 amino acid residues at the N and C terminus but does not contain a full length thymosin β4 amino acid sequence.

In one embodiment the polypeptide comprises the amino acid sequence provided in any one of SEQ ID NOs: 1-16 as the only active agent. In another embodiment the polypeptide consists essentially of the amino acid sequence provided in any one of SEQ ID NOs: 1-16.

In another embodiment the polypeptide comprises or consists essentially of oxidized TB4, N-terminal variants of Tβ4, C-terminal variants of Tβ4, polypeptides or peptide fragments comprising or consisting essentially of the amino acid sequence LKKTETQ (SEQ ID NO: 1), LKKTNTQ (SEQ ID NO: 17), KLKKTETQ (SEQ ID NO: 18), LKKTETQQ (SEQ ID NO: 19), LKKTET (SEQ ID NO: 20), conservative variants thereof.

International Application Serial No. PCT/US99/17282, incorporated herein by reference, discloses LKKTET (SEQ ID NO: 20) and isoforms of Tβ4 which may be useful in accordance with the present invention as well as amino acid sequence LKKTETQ (SEQ ID NO: 1) and conservative variants thereof, which may be utilized with the present invention.

International Application Serial No. PCT/GB99/00833 (WO 99/49883), incorporated herein by reference, discloses oxidized Tβ4 which may be utilized in accordance with the present invention.

Although the present invention is described primarily hereinafter with respect to SEQ ID NO: 1, it is to be understood that the following description is intended to be equally applicable to amino acid sequences provided as SEQ ID NOs: 2-20 and to Tβ4 and Tβ4 isoforms.

Many Tβ4 isoforms have been identified and have about 70%, or about 75%, or about 80% or more homology to the known amino acid sequence of Tβ34. Such isoforms include, for example, Tβ4$^{ala}$, Tβ9, Tβ10, Tβ11, Tβ12, Tβ13, Tβ14 and Tβ15. Thus, it is specifically contemplated that known Tβ4 isoforms, such as Tβ4$^{ala}$, Tβ9, Tβ10, Tβ11, Tβ12, Tββ13, Tβ14 and Tβ15, as well as Tβ4 isoforms not yet identified, will be useful in the methods of the invention. The invention therefore further provides a composition comprising Tβ4 or fragments or variants or Tβ4 isoforms Tβ4$^{ala}$, Tβ9, Tβ10, Tβ11, Tβ12, Tβ13, Tβ14 and Tβ15 or fragments or variants for treating type 2 diabetes.

In one embodiment the composition is a pharmaceutical composition and comprises a pharmaceutically acceptable carrier.

In another embodiment the composition is a veterinary composition and comprises a carrier suitable for veterinary use.

Laboratory techniques are well known for the preparation of peptides, such methods being readily performed by a skilled person; for example, using recombinant DNA technologies as set out in Sambrook et al (2001): Molecular cloning, a laboratory manual, 3$^{nd}$ edition, Cold Spring Harbor Press, Cold Spring Harbor, N.Y. Hence the skilled person can prepare thymosin polypeptides using the information provided herein and from common general knowledge.

Peptides and polypeptides used according to the invention may be subject to degradation by a number of means (such as protease activity in biological systems). Such degradation may limit the bioavailability of the polypeptides and hence the ability of the polypeptides to achieve their biological function. There are wide ranges of well-established techniques by which polypeptidesthat have enhanced stability in biological contexts can be designed and produced. Such polypeptides may have improved bioavailability as a result of increased resistance to protease-mediated degradation. Preferably, a variant suitable for use according to the invention is more protease-resistant than the polypeptide or peptide from which it is derived.

The N and/or C terminal of the polypeptide may be protected by a protecting group. For example, the N terminal may be protected by an acetyl group, or by an alkyl or aryl group, or an alkyl-CO— or aryl-CO— group, each of which may be optionally substituted. The C terminal may be protected by an amide group or by a substituted amide group.

In one embodiment the polypeptide has an N terminal acyl group and a C terminal hydroxyl group, for example Ac-SEQ ID NO: 1-OH.

The addition of a protecting group to the N and/or C terminus of the polypeptide may enhance the protease resistance of the peptide. Protease-resistance may be evaluated by means of well-known protein degradation assays. The relative values of protease resistance for the protected polypeptide and polypeptide may then be compared.

Peptoid derivatives of the polypeptides used in the invention may be readily designed from knowledge of the structure of the polypeptide. Commercially available software may be used to develop peptoid derivatives according to well-established protocols.

A further embodiment of a modified form of peptides used according to the invention comprises D-amino acid forms of the peptide. The preparation of peptides using D-amino acids rather than L-amino acids greatly decreases any unwanted breakdown of such an agent by normal metabolic processes, decreasing the amounts of agent which need to be administered, along with the frequency of its administration.

The peptides, fragments or variants used in the invention may be expressed by biological cells and the inventions include the use of such agents produced recombinantly.

The term "peptidomimetic" refers to a compound that mimics the conformation and desirable features of a particular peptide as a therapeutic agent, but that avoids the undesirable features. For example, morphine is a compound which can be orally administered, and which is a peptidomimetic of the peptide endorphin. There are a number of different approaches to the design and synthesis of peptidomimetics, as is well known in the art.

The peptides used in the invention can also contain further amino acid sequences which are not derived from the amino acid sequence thymosin: for example, other amino acid sequences which provide a separate function of the peptide (such as a tag, or a catalytic domain). The use of such peptides is also included in the aspects of the invention.

All peptides, polypeptides, fragments, variants, derivatives or peptidomimetics of thymosin or SEQ ID NO:1 or a variant thereof used in the invention are hereinafter referred to as therapeutic agent(s). Such therapeutic agents are all capable of treating type 2 diabetes.

As can be appreciated, the medicament may be administered to a variety of different subjects. By "subject" we include any animal that is susceptible to developing type 2 diabetes or who has the disease, preferably a vertebrate, more preferably a mammal such as a domesticated or farmyard animal or a human. Most preferably the subject is a human.

The therapeutic agent may be administered orally, topically, or parenterally in medicaments containing conventional non-toxic pharmaceutically acceptable carriers, adjuvants, and vehicles.

The term parenteral as used herein includes intravenous, intraarterial, intraperitoneal, intramuscular, subcutaneous, subconjunctival, intracavity, transdermal and subcutaneous injection, aerosol for administration to lungs or nasal cavity or administration by infusion by, for example, osmotic pump.

Various means by which a medicament comprising a therapeutic agent can be formulated are provided below.

The therapeutic agent may be formulated into compositions having a number of different forms depending, in particular on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle for the polypeptide should be one which is well tolerated by the subject to whom it is given, and preferably enables delivery of the therapeutic agents to the target cell, tissue, or organ.

Hence, it is preferred that that polypeptide is delivered by means of a suitably protected carrier particle, for example, a micelle.

The therapeutic agents may be used in a number of ways. For instance, systemic administration may be required in which case therapeutic agents may be contained within a composition which may, for example, be ingested orally in the form of a tablet, capsule or liquid. It is preferred that therapeutic agents are administered by injection into the blood stream. Injections may be intravenous (bolus or infusion) or subcutaneous (bolus or infusion).

Therapeutic agents may be presented in pharmaceutical compositions having a number of different forms depending, in particular on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle used to provide the treatment should be one which is well tolerated by the subject to whom it is given, and preferably enables delivery of the therapeutic to the target cell, tissue, or organ.

In a preferred embodiment, the pharmaceutical vehicle is a liquid and the pharmaceutical composition is in the form of a solution. In another embodiment, the pharmaceutical vehicle is a gel and the composition is in the form of a cream.

Therapeutic agents may also be incorporated within a slow or delayed release device. Such devices may, for example, be inserted on or under the skin, and the therapeutic agent may be released over weeks or even months. Such devices may be particularly advantageous when long term treatment with the therapeutic agents is required and which would normally require frequent administration (e.g. at least daily injection).

It will be appreciated that the amount of a therapeutic agent that is required is determined by its biological activity and bioavailability which in turn depends on the mode of administration, the physicochemical properties of the therapeutic agent employed, and whether the therapeutic agent is being used as a mono-therapy or in a combined therapy. Also, the amount will be determined by the number and state of target cells to be treated. The frequency of administration will also be influenced by the above-mentioned factors and particularly the half-life of the therapeutic agent within the subject being treated.

Optimal dosages to be administered may be determined by those skilled in the art, and will vary with the particular therapeutic agent in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of therapeutic agents and precise therapeutic regimes (such as daily doses of the therapeutic agents and the frequency of administration).

Daily doses may be given as a single administration. Alternatively, the therapeutic agents used may require administration twice or more times during a day. As an example, an therapeutic agents may be administered as two (or more depending upon the severity of the condition) daily doses of between 1 mg and 1000 mg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

In one embodiment the medicament comprising the therapeutic agent is administered subcutaneously or is formulated for subcutaneous administration to a subject. In one embodiment the medicament is an injectable composition.

In one embodiment the medicament is formulated to provide between 1 to 1000 mg of the therapeutic agent per administration. In one embodiment, the polypeptide is provided an amount from about 0.01 mg to about 10000 mg. In another embodiment, the amount of the peptide is an amount from about 0.1 mg to about 5000 mg. In another embodiment, the amount of the peptide is an amount from about 1 mg to about 1000 mg.

Methods of diagnosing type 2 diabetes are well known in the art; see, for example, <http://www.diabetes.org.uk/> which provides details of how type 2 diabetes is diagnosed; and potential treatments.

It is appreciated by the inventors that type 2 diabetes is commonly associated with a number of complications. For example, neuropathy, retinopathy, nephropathy, diabetic foot and ulcers, diabetic anaemia, and decrease in immune capacity. Therefore, the therapeutic agents disclosed herein in all aspects of the invention can be used to prevent or treat the underlying type 2 diabetes disorder itself, and also be used for the purpose of preventing or treating type 2 diabetes—associated disorders.

Accordingly, as used herein by "type 2 diabetes" all aspects of the invention also relate to the treatment of complications associated with this disorder; for example neuropathy, retinopathy, nephropathy, diabetic foot and ulcers, diabetic anaemia, and decrease in immune capacity.

It is also appreciated by the inventors that the medicaments disclosed herein in all aspects of the invention can be used alone or in combination with one or more additional medicament for preventing or treating type 2 diabetes. Examples of further medicaments include metformin and aspirin, while further medicament would be well known to the skilled person.

A fifth aspect of the invention provides a population of stem cells that secrete thymosin for use as a medicament for the prevention or treatment of type 2 diabetes.

The inventors have surprisingly identified that, when administered to a subject, stem cells which secrete thymosin can be effective therapeutic agents for the prevention or treatment of type 2 diabetes. Until the present disclosure, it had not been disclosed or suggested that such stem cells would have this utility.

Stem cells are cells that have the potential to differentiate into a number of cell types in the body. Theoretically, stem cells may divide without limit to replenish other cells for as long as the organism is alive. Upon differentiation, the daughter cell has the potential to remain a stem cell or become another cell type, for example lung cell and display its characteristics, thus holding promise for many diseases by replacing damaged tissues. These phenomena may be induced under specific physiological and experimental conditions.

In general, stem cell therapy represents a therapeutic method by which degenerative and/or progressive diseases (such as those caused by premature death or malfunction of cell types that the body is unable to replace) may be treated. It is hoped that addition of stem cells may help nucleate and promote the development of functional cells and/or tissues to replace those lost, thereby restoring normal healthy activity/function.

For the purposes of the present invention, "stem cells" are taken to comprise nullipotent, totipotent or pluripotent cells, and progenitor cells (or precursor cells) to comprise multipotent cells. For the avoidance of doubt, the medicament and methods of the invention can comprise a therapeutically effective quantity of either stem or progenitor cells, or both stem and progenitor cells. Preferred culture conditions for use in accordance with the present invention may be determined with reference to the type of biological cell to be cultured. Consideration should be given both to the nature of the cell (e.g. stem or progenitor cell), to the source of the cell, and also to the manner in which the cell is to be utilised. Suitable culture conditions are well known to those skilled in the art.

A suitable source of stem cells that may be used in accordance with the present invention are cells derived from the inner cell mass/epiblast of pre-implantation embryos. Such embryonic stem (ES) cells are readily obtainable and are capable of giving rise to all possible embryonic and adult cell lineages. In particular, the undifferentiated human ESC (H1 line from WiCell Research Institute, Inc, Madison, Wis.: <www.wicell.org>) could be used in the invention; this cell line is commercially available. A further source of stem cells that can be used in the present invention are umbilical cord-derived cells. A still further source of stem cells are those isolated from adult tissues, including adipose tissues.

Where the medicament of the invention involves the use of biological cells, preferably the formulation for comprises biological cells in a suitable liquid carrier. Such a liquid carrier is preferably non-immunogenic, and may comprise a saline solution, cell culture medium, or distilled water. Formulations for injection may be as described above, or may also be provided in the form of a gel, which may preferably be capable of resolution by the body of the subject treated. Formulations suitable for implantation may take the forms described for injection or inhalation, and may also comprise biological cells provided in a scaffold or matrix capable of providing a foundation for new tissue development.

A further aspect of the invention provides a method of treating type 2 diabetes comprising supplying to a subject a therapeutically effective quantity of thymosin, or a fragment, variant or derivative thereof, and/or a population of stem cells that secrete thymosin.

By "thymosin, or a fragment, variant or derivative thereof, and/or a population of stem cells" we include all those particular embodiments discussed above in relation to other aspects of the invention.

The terms "treating" and "treatment" as used herein refer to reduction in severity and/or frequency of symptoms, elimination of symptoms and/or underlying cause, prevention of the occurrence of symptoms (prophylaxis) and/or their underlying cause, and improvement or remediation of damage. Thus, for example, the present method of "treating" a disorder encompasses both prevention of the disorder in a predisposed individual and treatment of the disorder in a clinically symptomatic individual.

"Treating" as used herein covers any treatment of, or prevention of a condition in a vertebrate, a mammal, particularly a human, and includes: inhibiting the condition, i.e., arresting its development; or relieving or ameliorating the effects of the condition, i.e., cause regression of the effects of the condition.

"Prophylaxis" or "prophylactic" or "preventative" therapy or "prevent" or "prevention" as used herein includes preventing the condition from occurring or ameliorating the subsequent progression of the condition in a subject that may be predisposed to the condition, but has not yet been diagnosed as having it.

In one embodiment the method or composition prevents or slows progression of type 2 diabetes or prevents or slows progression from glucose intolerance to type 2 diabetes. In another embodiment the method or composition lessens the symptoms of type 2 diabetes or associated disorders. In another embodiment the method or composition improves glucose tolerance in subjects with type 2 diabetes. In another embodiment the method or composition improve quality of life for subjects with type 2 diabetes. In another embodiment the method or composition prolong life span in subjects with type 2 diabetes.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is now further described in detail by reference to the following example. The example is provided for purposes of illustration only, and is not intended to be limiting unless otherwise specified. Thus, the invention encompasses any and all variations which become evident as a result of the teaching provided herein.

Example 1

Treatment of Type 2 Diabetes

An injectable pharmaceutical composition can be prepared having between 1 to 1000 mg of a thymosin fragment consisting of the amino acid sequence LKKTETQ (SEQ ID NO1). The composition is then administered to the subject subcutaneously.

Example 2

TB4-7 Trial

The inventors have performed a single-center, randomized, double-blind, placebo-controlled 2-month trial of twice a week s.c. injection of 10 mg of TB4-7 (a peptide having the amino acid sequence LKKTETQ (SEQ ID NO:1)) in type 2 diabetic patients inadequately treated with diet/lifestyle or stable doses of common hypoglycemics for at least 3 months. The results from an interim 2 month report of that trial is provided in this example.

Patients with type 2 diabetes for >/=1 year were entered into 2 strata of hemoglobin A(1c) (HbA(1c)) levels: Stratum 1: 8.0% to 9.9%; and Stratum 2: 10.0% to 12.0%.

All subjects began a 1-month single-blind placebo run-in phase, followed by randomization in a 2:1 ratio of active treatment: placebo, to 2 months of double-blind treatment with either TB4-7 or saline placebo. Concurrent oral agents were continued unchanged throughout the study.

The primary outcome was the change in HbA(1c) from randomization; results of each stratum were analyzed independently. The baseline characteristics of 26 subjects who completed the study were comparable between treatment groups. 14 subjects entered stratum 1 and 12 entered stratum 2.

A statistically significant reduction of HbA(1c) from randomization to end-of-study was seen in the stratum 2 subjects:

TB4-7: 11.1%+/−1.0% to 8.0%+/−1.9%, P=0.004;

Placebo: 10.8%+/−1.4% to 11.2%+/−1.8%, not significant [NS].

No significant HbA(1c) reductions were seen in the stratum 1 subjects.

There were no significant treatment-related differences in the fasting plasma glucose (FPG) and this may be due to the small number of candidates used. However, a significant increase in quality of life indices was observed in the TB4-7 group.

Lipids, body mass index (BMI), body composition, blood pressure, insulin sensitivity estimates using the minimal model, glucose and insulin responses to a meal challenge were not calculated.

No adverse events, or other safety indices between treatment groups were observed. From this data it can be seen that TB4-7 was well tolerated. Twice weekly treatment with TB4-7 for 2 months significantly improved glucose control in type 2 diabetic patients with HbA(1c) levels between 10.0% to 12.0%.

In conclusion this study represents the first prospective intervention trial of therapy with a TB4 derivative for intermediate-term glucose control in type 2 diabetes. Hence the study supports the use of a TB4 derivative as a medicament for the treatment of type 2 diabetes.

Example 3

Dog Diabetes Mellitus Trials

The inventors have further investigated the utility of TB4 and derivatives of that protein as a medicament for the treatment of type 2 diabetes. The data from that study is provided below.

Criteria for Selection of Cases

A total of 48 dogs took part in the trials. Dogs where put into two groups of 24: one group was injected with the full 10 mg Thymosin beta 4 protein (TB4) once a week; and the other group was injected with 10 mg TB4-7 once a week for four weeks.

Diagnosis criteria of DM and the pre-requisites for study inclusion were:

(1) clinical signs consistent with canine DM, such as polydipsia, polyuria, polyphagia, and weight loss; (2) persistent and 24-hour fasting hyperglycemia (>200 mg/dL) for more than 2 days; (3) persistent glycosuria for more than 2 days; and (4) insulin supplementation required to maintain normal glucose levels.

Glycosylated hemoglobin and blood glucose levels where measured at before every injection and seven days after the last injection.

TABLE 1

|  | TB4 | | TB4-7 | |
|---|---|---|---|---|
|  | Glucose | HbA1c | Glucose | HbA1c |
| Week 0 | 298 ± 64 | 7.7 ± 2.2 | 289 ± 71 | 7.9 ± 2.3 |
| Week 1 | 310 ± 78 | 7.8 ± 2.3 | 278 ± 73 | 7.6 ± 2.3 |
| Week 2 | 296 ± 64 | 7.7 ± 2.2 | 262 ± 81 | 7.1 ± 2.5 |
| Week 3 | 275 ± 72 | 7.2 ± 2.6 | 189 ± 76 | 6.3 ± 2.5 |
| Week 4 | 213 ± 82 | 6.1 ± 2.9 | 175 ± 74 | 5.2 ± 2.6 |

Glucose (mg/dL)
HbA1c (%)

---

The invention claimed is:

1. A method of improving glycemic control in a subject having type 2 diabetes, comprising administering to the subject an effective amount of a peptide of an amino acid sequence selected from the group consisting of LKKTETQ (SEQ ID NO:1), FDKSKLKKTETQEKN (SEQ ID NO:4), FDKAKLKKTETQEKN (SEQ ID NO:5), FDKTKLKK-TETQEKN (SEQ ID NO:7), and FNRAKLKKTETQEKN (SEQ ID NO:11), to improve glycemic control, wherein the peptide comprises at least one modification selected from the group consisting of at least one D-amino acid residue, an N-terminal acyl modification, a C-terminal hydroxyl modification, and both an N-terminal acyl modification and a C-terminal hydroxyl modification.

2. The method of claim 1, wherein the peptide comprises at least one D-amino acid residue.

3. The method of claim 1 or 2, wherein the peptide comprises an N-terminal acyl modification.

4. The method of claim 1 or 2, wherein the peptide comprises a C-terminal hydroxyl modification.

5. The method of claim 1 or 2, wherein the peptide comprises an N-terminal acyl modification and a C-terminal hydroxyl modification.

6. A method of improving glycemic control in a subject having type 2 diabetes, comprising administering to the subject an effective amount of a peptide consisting of LKKTETQ (SEQ ID NO:1) to improve glycemic control, wherein the peptide comprises at least one modification selected from the group consisting of at least one D-amino acid residue, an N-terminal acyl modification, a C-terminal hydroxyl modification, and both an N-terminal acyl modification and a C-terminal hydroxyl modification.

7. The method of claim 6, wherein the peptide comprises at least one D-amino acid residue.

8. The method of claim 6 or 7, wherein the peptide comprises an N-terminal acyl modification.

9. The method of claim 6 or 7, wherein the peptide comprises a C-terminal hydroxyl modification.

10. The method of claim 6 or 7, wherein the peptide comprises an N-terminal acyl modification and a C-terminal hydroxyl modification.

* * * * *

SEQUENCE LISTING

```
<160> NUMBER OF SEQ ID NOS: 20

<210> SEQ ID NO 1
<211> LENGTH: 7
<212> TYPE: PRT
<213> ORGANISM: Homo sapiens

<400> SEQUENCE: 1

Leu Lys Lys Thr Glu Thr Gln
1               5

<210> SEQ ID NO 2
<211> LENGTH: 44
<212> TYPE: PRT
<213> ORGANISM: Homo sapiens

<400> SEQUENCE: 2

Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
                20                  25                  30

Glu Thr Ile Glu Gln Glu Lys Gln Ala Gly Glu Ser
            35                  40

<210> SEQ ID NO 3
<211> LENGTH: 37
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: Each Xaa can be any naturally occurring amino
      acid, and any one or more can be absent
<220> FEATURE:
<221> NAME/KEY: MISC_FEATURE
<222> LOCATION: (18)..(18)
<223> OTHER INFORMATION: Xaa can be any naturally occurring amino acid
<220> FEATURE:
<221> NAME/KEY: MISC_FEATURE
```

```
<222> LOCATION: (20)..(22)
<223> OTHER INFORMATION: Each Xaa can be any naturally occurring amino
      acid
<220> FEATURE:
<221> NAME/KEY: MISC_FEATURE
<222> LOCATION: (23)..(37)
<223> OTHER INFORMATION: Each Xaa can be any naturally occurring amino
      acid, and any one or more can be absent

<400> SEQUENCE: 3

Xaa Xaa Xaa Xaa Xaa Xaa Xaa Xaa Xaa Xaa Xaa Xaa Xaa Xaa Leu
1               5                   10                  15

Lys Xaa Thr Xaa Xaa Xaa Xaa Xaa Xaa Xaa Xaa Xaa Xaa Xaa Xaa
            20                  25                  30

Xaa Xaa Xaa Xaa Xaa
        35

<210> SEQ ID NO 4
<211> LENGTH: 15
<212> TYPE: PRT
<213> ORGANISM: Homo sapiens

<400> SEQUENCE: 4

Phe Asp Lys Ser Lys Leu Lys Lys Thr Glu Thr Gln Glu Lys Asn
1               5                   10                  15

<210> SEQ ID NO 5
<211> LENGTH: 15
<212> TYPE: PRT
<213> ORGANISM: Homo sapiens

<400> SEQUENCE: 5

Phe Asp Lys Ala Lys Leu Lys Lys Thr Glu Thr Gln Glu Lys Asn
1               5                   10                  15

<210> SEQ ID NO 6
<211> LENGTH: 15
<212> TYPE: PRT
<213> ORGANISM: Homo sapiens

<400> SEQUENCE: 6

Phe Asp Arg Ser Lys Leu Lys Lys Thr Glu Thr Asn Thr Glu Glu
1               5                   10                  15

<210> SEQ ID NO 7
<211> LENGTH: 15
<212> TYPE: PRT
<213> ORGANISM: Homo sapiens

<400> SEQUENCE: 7

Phe Asp Lys Thr Lys Leu Lys Lys Thr Glu Thr Gln Glu Lys Asn
1               5                   10                  15

<210> SEQ ID NO 8
<211> LENGTH: 15
<212> TYPE: PRT
<213> ORGANISM: Homo sapiens

<400> SEQUENCE: 8

Phe Asp Lys Ser Lys Leu Lys Lys Thr Asn Thr Glu Glu Lys Asn
1               5                   10                  15

<210> SEQ ID NO 9
<211> LENGTH: 15
<212> TYPE: PRT
```

<213> ORGANISM: Homo sapiens

<400> SEQUENCE: 9

Phe Asp Arg Ser Lys Leu Lys Lys Thr Asn Thr Glu Glu Lys Asn
1               5                   10                  15

<210> SEQ ID NO 10
<211> LENGTH: 15
<212> TYPE: PRT
<213> ORGANISM: Homo sapiens

<400> SEQUENCE: 10

Phe Asp Lys Thr Lys Leu Lys Lys Thr Glu Thr Ala Glu Lys Asn
1               5                   10                  15

<210> SEQ ID NO 11
<211> LENGTH: 15
<212> TYPE: PRT
<213> ORGANISM: Homo sapiens

<400> SEQUENCE: 11

Phe Asn Arg Ala Lys Leu Lys Lys Thr Glu Thr Gln Glu Lys Asn
1               5                   10                  15

<210> SEQ ID NO 12
<211> LENGTH: 15
<212> TYPE: PRT
<213> ORGANISM: Homo sapiens

<400> SEQUENCE: 12

Phe Asn Lys Ala Lys Leu Lys Lys Thr Glu Met Gln Glu Lys Asn
1               5                   10                  15

<210> SEQ ID NO 13
<211> LENGTH: 15
<212> TYPE: PRT
<213> ORGANISM: Homo sapiens

<400> SEQUENCE: 13

Phe Asp Ala Lys Lys Leu Lys His Thr Glu Thr Asn Glu Lys Asn
1               5                   10                  15

<210> SEQ ID NO 14
<211> LENGTH: 15
<212> TYPE: PRT
<213> ORGANISM: Homo sapiens

<400> SEQUENCE: 14

Phe Asn Gln Asn Asn Leu Lys His Thr Glu Thr Asn Glu Lys Asn
1               5                   10                  15

<210> SEQ ID NO 15
<211> LENGTH: 15
<212> TYPE: PRT
<213> ORGANISM: Homo sapiens

<400> SEQUENCE: 15

Leu Asp Lys Ala Lys Leu Lys Ala Thr Glu Met Gln Glu Lys Asn
1               5                   10                  15

<210> SEQ ID NO 16
<211> LENGTH: 15
<212> TYPE: PRT
<213> ORGANISM: Homo sapiens

```
<400> SEQUENCE: 16

Phe Asp Lys Ala Gly Leu Lys Lys Thr Glu Thr Glu Glu Lys Glu
1               5                   10                  15

<210> SEQ ID NO 17
<211> LENGTH: 7
<212> TYPE: PRT
<213> ORGANISM: Homo sapiens

<400> SEQUENCE: 17

Leu Lys Lys Thr Asn Thr Gln
1               5

<210> SEQ ID NO 18
<211> LENGTH: 8
<212> TYPE: PRT
<213> ORGANISM: Homo sapiens

<400> SEQUENCE: 18

Lys Leu Lys Lys Thr Glu Thr Gln
1               5

<210> SEQ ID NO 19
<211> LENGTH: 8
<212> TYPE: PRT
<213> ORGANISM: Homo sapiens

<400> SEQUENCE: 19

Leu Lys Lys Thr Glu Thr Gln Gln
1               5

<210> SEQ ID NO 20
<211> LENGTH: 6
<212> TYPE: PRT
<213> ORGANISM: Homo sapiens

<400> SEQUENCE: 20

Leu Lys Lys Thr Glu Thr
1               5
```